United States Patent
Ko et al.

(10) Patent No.: US 7,610,170 B2
(45) Date of Patent: Oct. 27, 2009

(54) METHOD FOR ENHANCING THE MEASUREMENT CAPABILITY OF MULTI-PARAMETER INSPECTION SYSTEMS

(75) Inventors: Chun Hung Ko, Changhua County (TW); Yi Sha Kuo, Hsinchu (TW); Chung Chu Chang, Taipei (TW)

(73) Assignee: Industrial Technology Research Institute, Hsinchu County (TW)

( * ) Notice: Subject to any disclaimer, the term of this patent is extended or adjusted under 35 U.S.C. 154(b) by 9 days.

(21) Appl. No.: 11/858,442

(22) Filed: Sep. 20, 2007

(65) Prior Publication Data

US 2009/0030631 A1    Jan. 29, 2009

(30) Foreign Application Priority Data

Jul. 27, 2007    (TW) ................ 96127431 A

(51) Int. Cl.
    *G06F 19/00*    (2006.01)
(52) U.S. Cl. ...................... 702/179; 702/180
(58) Field of Classification Search ............ 250/339.01; 702/83, 179, 180; 706/902, 911, 912
    See application file for complete search history.

(56) References Cited

U.S. PATENT DOCUMENTS 6,900,892 B2 *   5/2005   Shchegrov et al. .......... 356/369
7,099,005 B1 *   8/2006   Fabrikant et al. ............ 356/369

OTHER PUBLICATIONS

"Formulation for Stable and Efficient Implementation of the Rigorous Coupled-Wave Analysis of Binary Gratings"; Moharam, MG; Grann,EB; Pommet, DA; Journal of the Optical Society of America; vol. 12, issue 5; May 1995; pp. 1068-1076.*

Thomas Hingst et al.,; Spectroscopic ellipsometry-based scatterometry for depth and line width measurements of plysilicon-filled deep trenches; Journal; 2004; pp. 587-596; vol. 5375; Metrology, Inspection, and Process Control for Microlithography XVIII; Proceedings of SPIE.

Vladimir A. Ukraintsev et al.,; A Comprehensive Test of Optical Scatterometry Readiness for 65 nm Technology Production; Jouranl; 2006; pp. 1-13; vol. 6152; Metrology, Inspection, and Process Control for Microlithography XX; Proceedings of SPIE.

* cited by examiner

*Primary Examiner*—Edward R Cosimano
*Assistant Examiner*—Douglas N Washburn
(74) *Attorney, Agent, or Firm*—WPAT, P.C.; Anthony King

(57) ABSTRACT

A method for improving the measurement capability of multi-parameter inspection systems includes performing a measuring procedure to acquire a measured signature of a sample, calculating weighting factors representing a correlation between structural parameters of the sample by using a weighting algorithm, transforming the weighting factors into a sampling function by using a transforming rule, updating the measured signature to form an updated measured signature and generating a plurality of updated nominal signatures according to the sampling function, and comparing the updated measured signature and the updated nominal signatures to determine the structural parameters of the sample.

30 Claims, 10 Drawing Sheets

METHOD FOR ENHANCING THE MEASUREMENT CAPABILITY OF MULTI-PARAMETER INSPECTION SYSTEMS

BACKGROUND OF THE INVENTION (A) Field of the Invention

The present invention relates to multi-parameter inspection systems, and more particularly, to a method for enhancing the measurement capability of multi-parameter inspection systems.

(B) Description of the Related Art

Multi-parameter inspection systems such as spectrometers, ellipsometers and scatterometers are very important inspection devices, and are widely used in several fields such as the semiconductor industry, the thin film optics and the optical communication industry.

Multi-parameter inspection systems, which measure more than one parameter simultaneously, analyze a set of measured signals to obtain values of each parameter at the same time. Practically, however, these parameters are not independent, therefore there is likely to be an incorrect measurement in the results due to a correlation between parameters. If such correlation exists, it will not only affect the accuracy of the obtained value but will reduce the precision of the inspection system as well.

"Spectroscopic ellipsometry-based scatterometry for depth and line width measurements of polysilicon-filled deep trenches" by Thomas Hingst, et al. (Metrology, Inspection, and Process Control for Microlithography XVIII, edited by Richard M. Silver, Proceedings of SPIE Vol. 5375, 2004) reported that how to avoid parameter correlation is a very important issue.

Also, "A Comprehensive Test of Optical Scatterometry Readiness for 65 nm Technology Production" by Vladimir A. Ukraintsev (Metrology, Inspection, and Process Control for Microlithography XX, edited by Chas N. Archie, Proc. of SPIE Vol. 6152, 61521G, 2006) reported that a solution to the problem of parameter correlation would be of great value.

However, these two papers did not provide a proper solution to the problem of parameter correlation. In short, as the related manufacturing process technology has developed, the standard of the accuracy and precision of inspection systems has become higher, so it has become more important to solve the long existing but often neglected problem of parameter correlation.

SUMMARY OF THE INVENTION

One exemplary example consistent with the present invention provides a method for enhancing the measurement capability of multi-parameter inspection systems. This exemplary method decreases sampling density of the measured signal in a high-correlation region and increases such sampling density in a low-correlation to reduce the influence of parameter correlation.

A method for enhancing the measurement capability of multi-parameter inspection systems according to this example of the present invention comprises the steps of performing a measuring procedure to acquire a measured signature of a sample, calculating a plurality of weighting factors representing a correlation between structural parameters of the sample by using a weighting algorithm, transforming the weighting factors into a sampling function by using a transforming rule, updating the measured signature to form an updated measured signature and a plurality of updated nominal signatures according to the sampling function, and comparing the updated measured signature and the nominal signatures to determine the structural parameters of the sample.

Another exemplary example consistent with the present invention provides a method for enhancing the measurement capability of multi-parameter inspection systems comprising performing a measuring procedure to acquire a measured signature of a sample, calculating a plurality of weighting factors representing a correlation between structural parameters of the sample by using a weighting algorithm, generating a sampling function with sampling numbers corresponding to the weighting factors, performing another measuring procedure to acquire an updated measured signature of the sample and generating a plurality of nominal signatures according to the sampling numbers of the sampling function, and comparing the updated measured signature and the nominal signatures to determine structural parameters of the sample.

A further exemplary example consistent with the present invention provides a multi-parameter inspection system comprising a nominal signature-generating module configured to generate a plurality of nominal signatures according to predetermined values for the structural parameters of a sample, a calculating module configured to calculate weighting factors representing a correlation between the structural parameters of the sample, a sampling module configured to update a sampling number according to the weighting factors, a measuring module configured to acquire a measured signature of the sample according to the sampling number, and a comparing module configured to determine the structural parameters of the sample according to the measured signature and the nominal signatures.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 1:
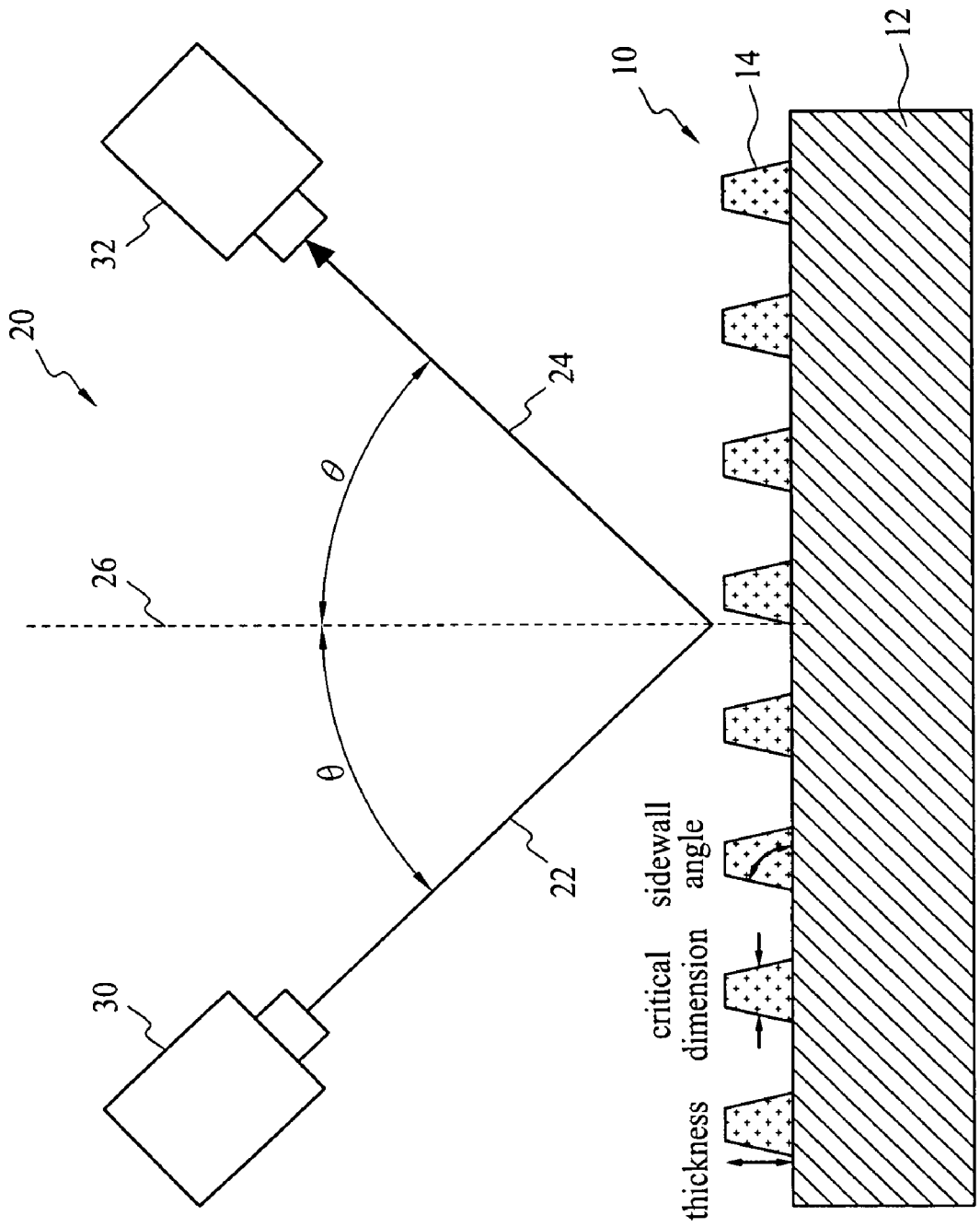
FIG. 1 shows a schematic view of a scatterometer measuring a sample.

FIG. 1 shows a schematic view of a scatterometer 20 measuring a sample 10. The sample 10 includes a substrate 12 and a grating 14 made of silicon nitride. The desired structural parameters include critical dimension, thickness and sidewall angle. Although this embodiment of the present invention is applied to a scatterometer, it can also be applied to other apparatuses such as spectroscopic reflectormeters and specular spectroscopic ellipsometers.

The scatterometer 20 adopts an optical architecture configured to scan different angles of a single waveform incidence. The optical detector 32 only receives the zero order diffraction light 24. Therefore, the included angle between the incident light 22 of a laser light source 30 and the normal 26 equals that between the zero order diffraction light 24 and the normal 26. The laser light source 30 could be a commonly used laser such as an argon laser (waveform 488 nm and 514 nm), a He—Cd laser (waveform 442 nm), a He—Ne laser (waveform 612), or an Nd-YAG laser (waveform 532 nm). By varying an incident angle θ, a diffraction spectrum, also called as a signature, of the angle of the incident light and the intensity of the zero order diffraction light 24 can be obtained, wherein the angle of the incident light is between +47 degrees and −47 degrees. In particular, this spectrum is a diffraction signature of the polarized light including s-polarized light and p-polarized light.

Figure 2A:
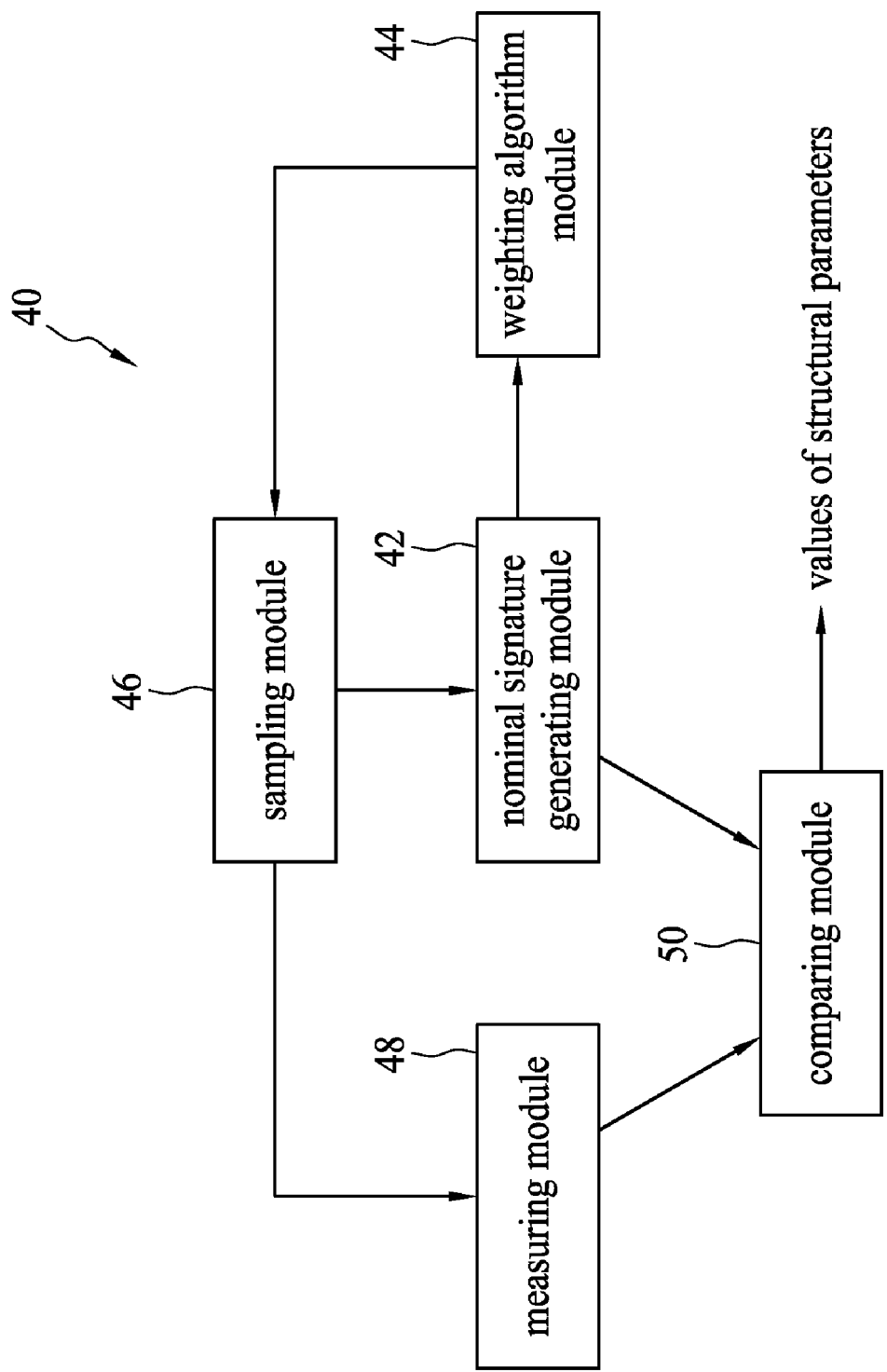
FIGS. 2(a) and 2(b) show a multi-parameter inspection system and the flow chart of a method for enhancing the measurement capability of the multi-parameter inspection system of the present invention.
Figure 2B:
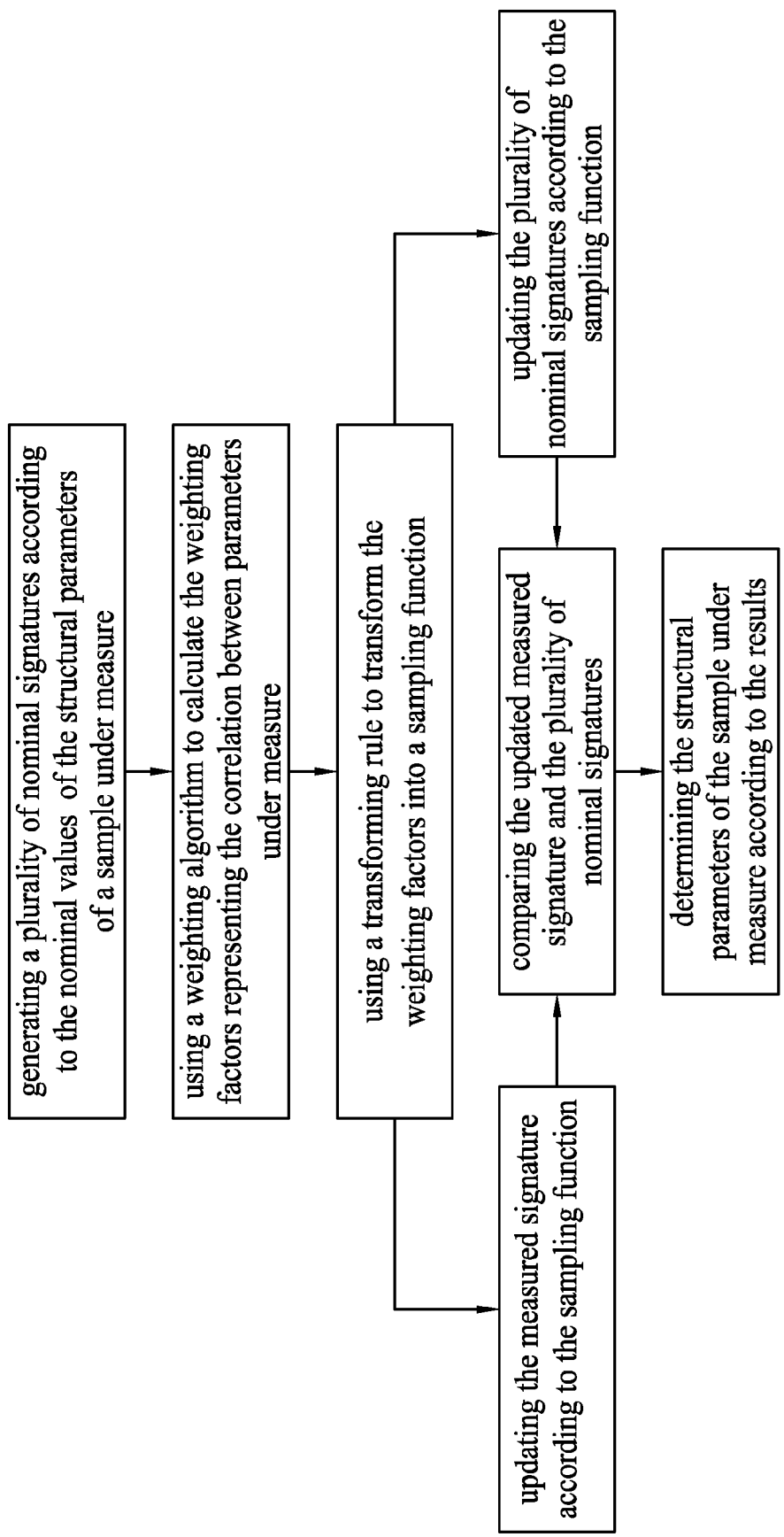
Figure 3A:
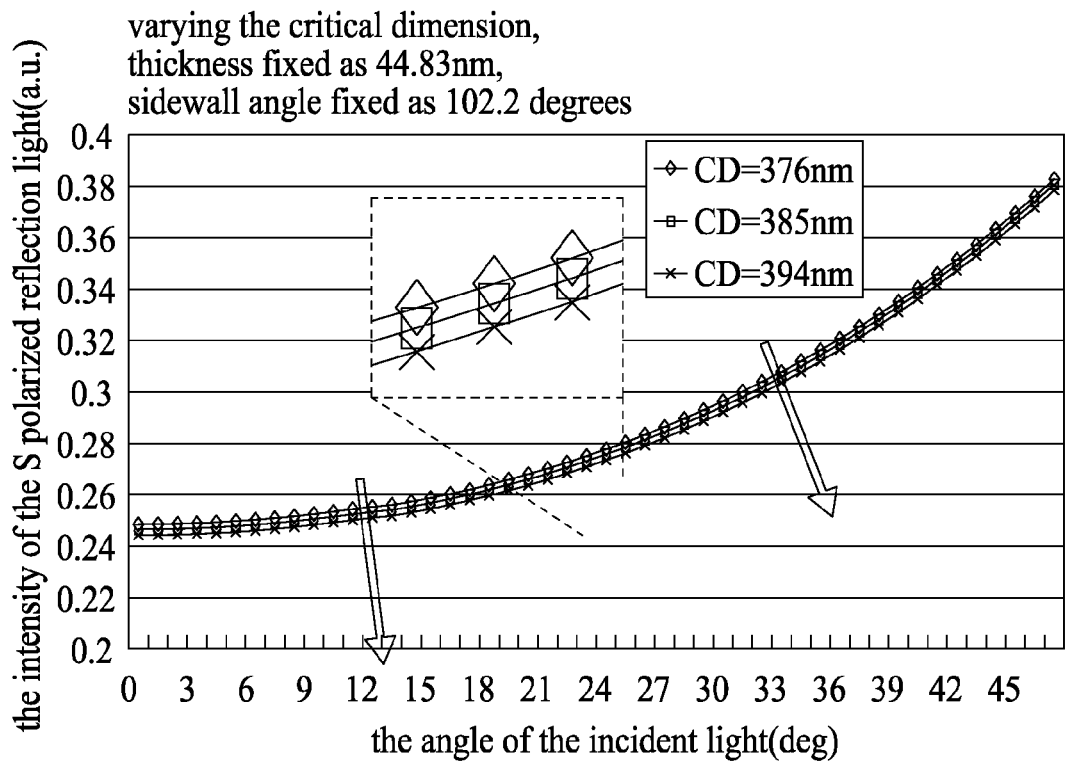
FIGS. 3(a), 3(b), 4(a), 4(b), 5(a) and 5(b) are the nominal signatures of the sample under different critical dimensions, thicknesses, and sidewall angles.
Figure 3B:
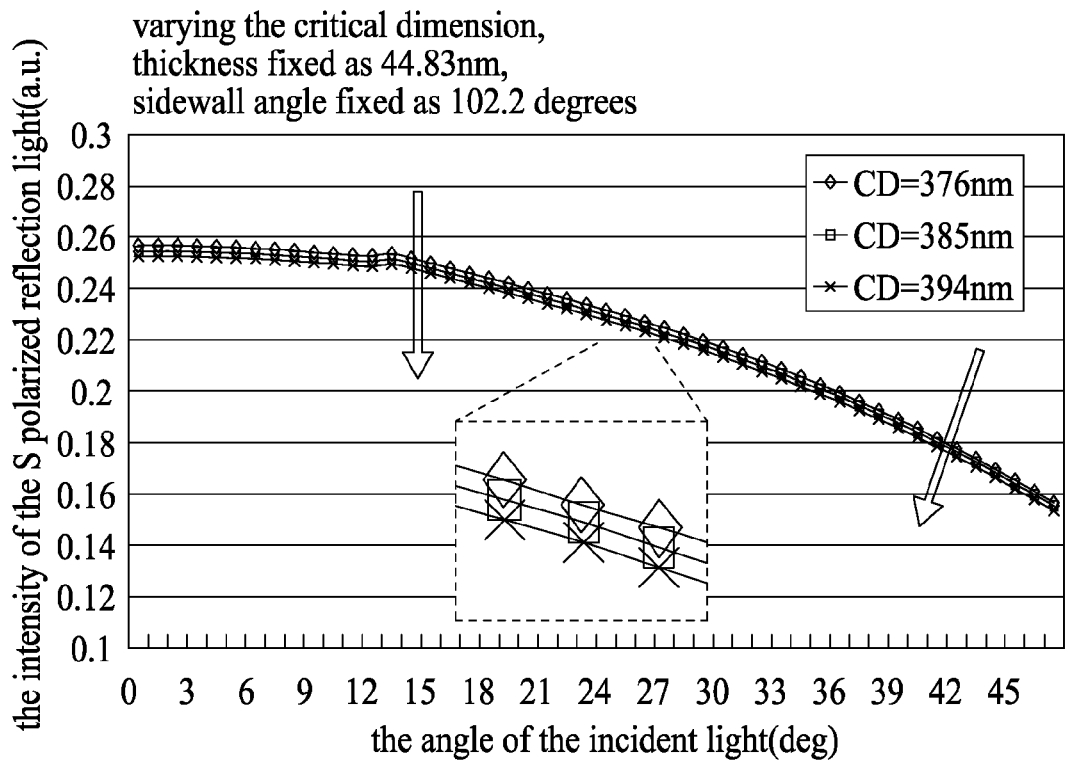
Figure 4A:
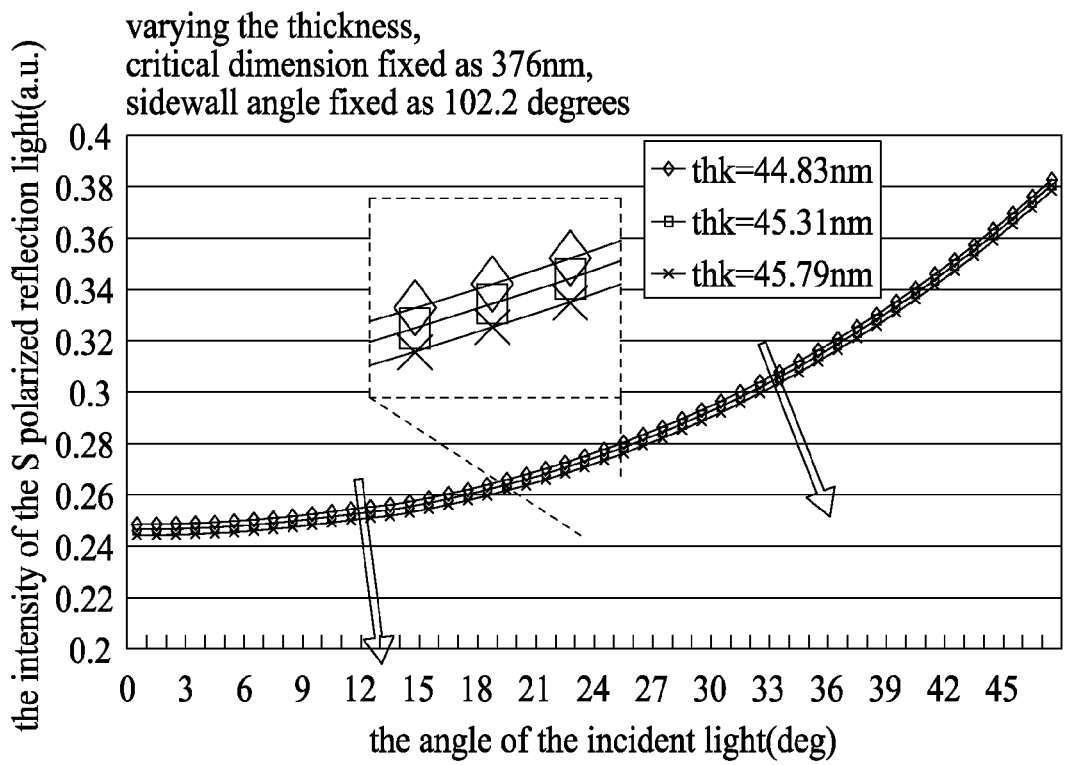
Figure 4B:
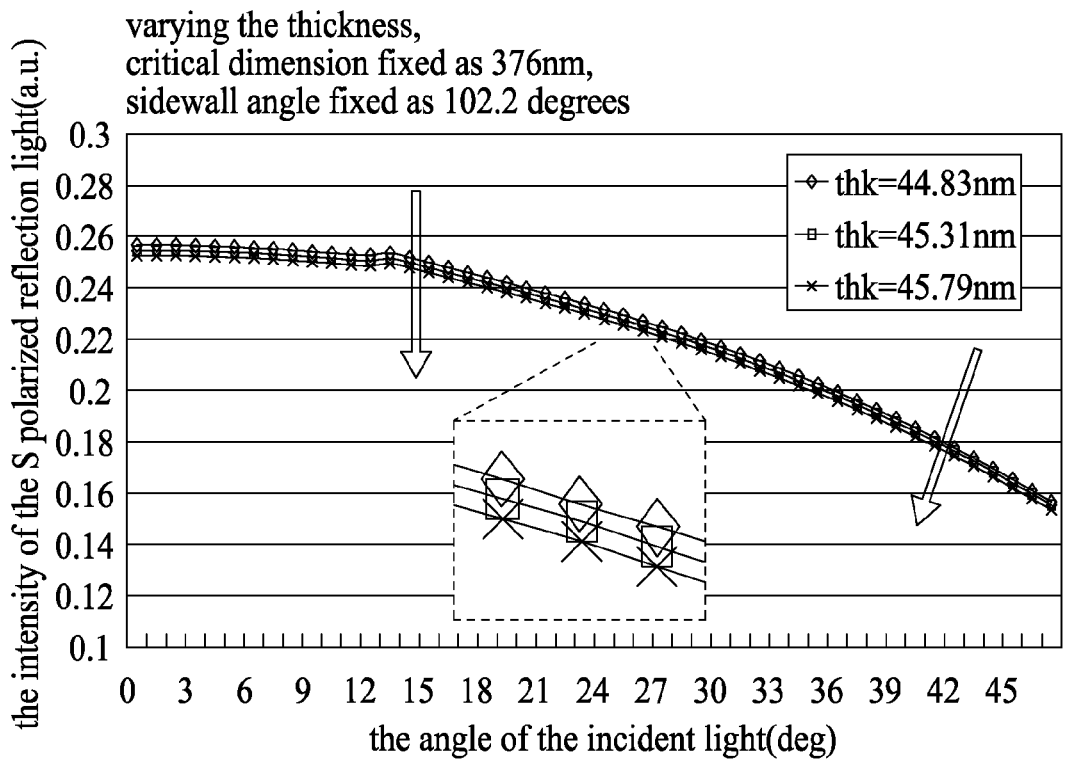
Figure 5A:
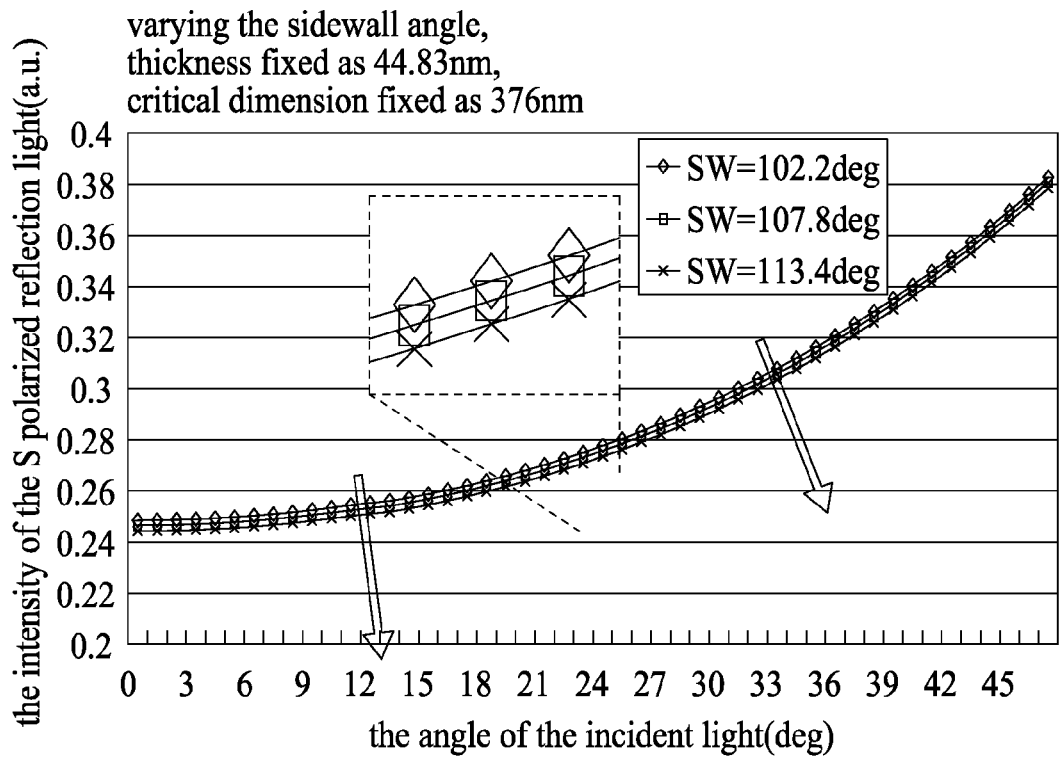
Figure 5B:
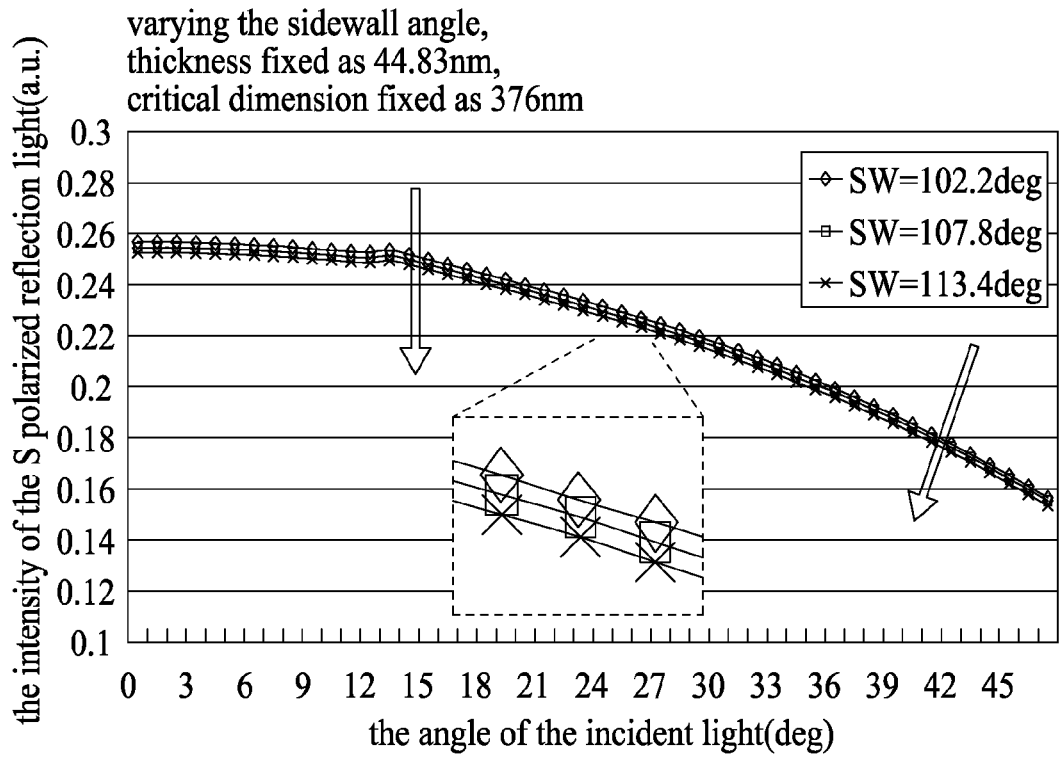

FIGS. 2(a) and 2(b) show a multi-parameter inspection system 40 and a flow chart for enhancing the measurement capability of the multi-parameter inspection system 40 according to one embodiment of the present invention. First, a nominal signature-generating module 42 generates a plurality of nominal signatures according to nominal structural values of a sample 10. A sampling module 48 performs a sampling procedure to acquire a measured signature of the sample 10. A calculating module is configured to calculate weighting factors representing a correlation between the structural parameters of the sample 10 by using a weighting algorithm. Subsequently, a sampling module 46 transforms the weighting factors into a sampling function by using a transforming rule. The nominal signature-generating module 42 and the measuring module 48 are configured to update the measured signature and the nominal signatures according to the sampling function. Finally, a comparing module 50 compares the updated measured signature and the updated nominal signatures to determine structural parameters of the sample 10.

FIGS. 3(a), 3(b), 4(a), 4(b), 5(a) and 5(b) show the nominal signatures of the sample 10 under different critical dimensions, thicknesses, and sidewall angles. These nominal signatures, which include s-polarized light signatures and p-polarized light signatures, are calculated by the nominal values of the sample 10, and vary with the different values of each parameter. Because these signatures are based on zero degrees of the incident light, they are symmetric on either side, and therefore FIGS. 3(a), 3(b), 4(a), 4(b), 5(a) and 5(b) only show the reflection light signatures between 0 degrees to 47 degrees. As the values of critical dimension, thickness, and sidewall angle increases, the tendency of the variation of these signatures is very similar. More specifically, the regions in FIGS. 3(a), 3(b), 4(a), 4(b), 5(a) and 5(b) indicated by arrows represent high correlation between each parameter.

Figure 6:
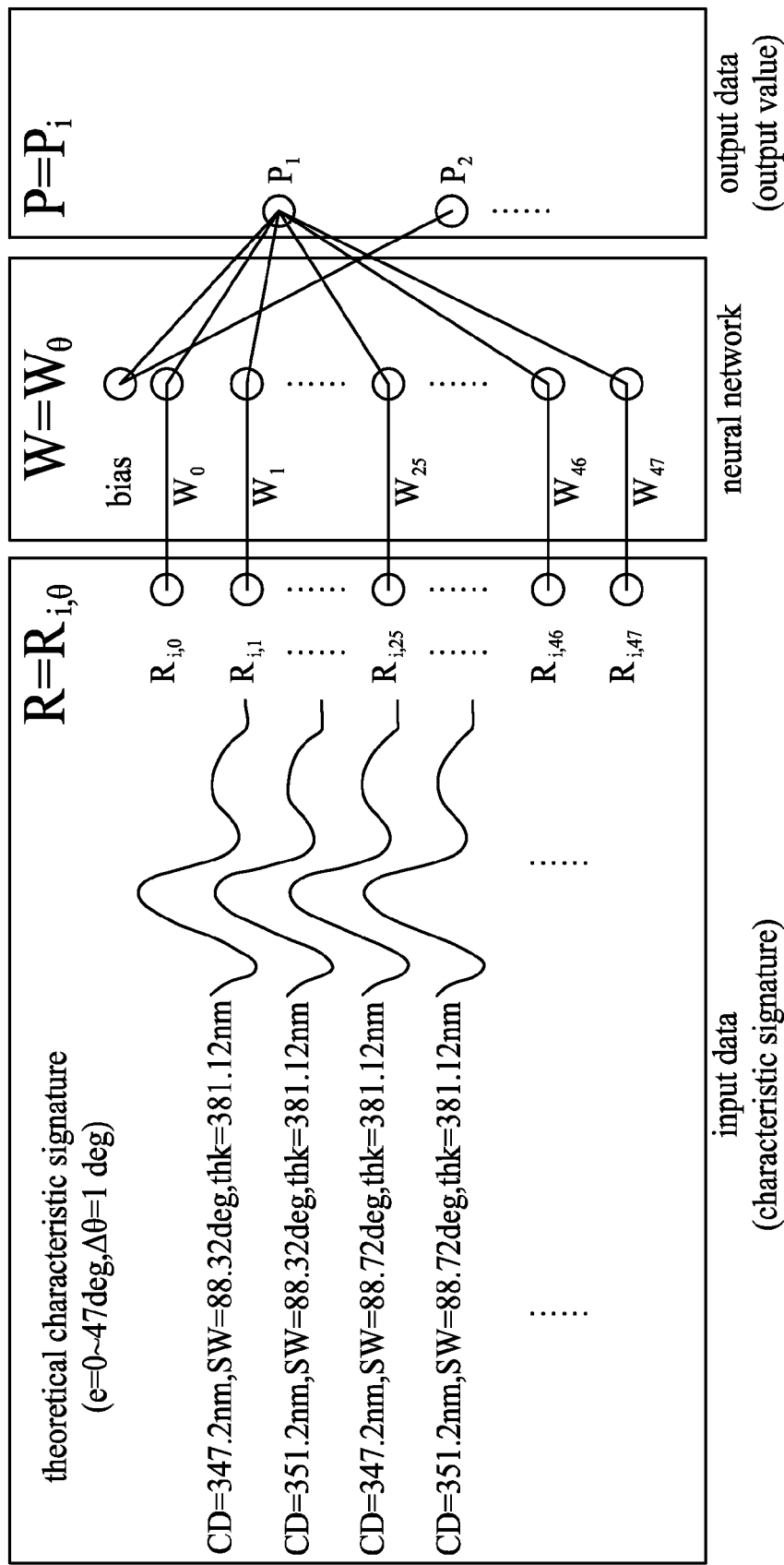
FIGS. 6 and 7 show a schematic diagram of the artificial neural network algorithm of the present invention and weighting factors calculated by that algorithm.
Figure 7:
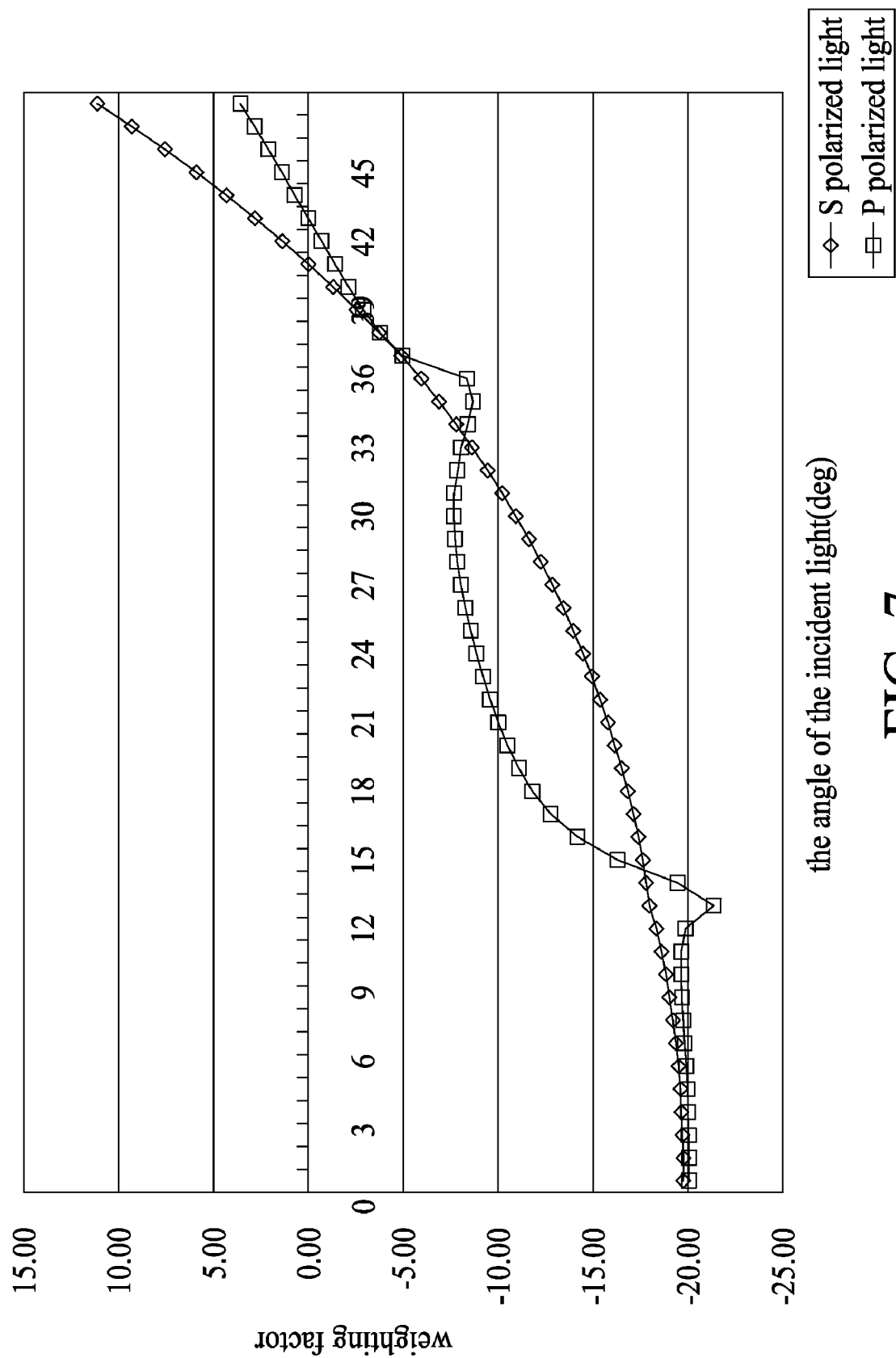

FIG. 6 shows the schematic diagram of the artificial neural network algorithm which is used to calculate the weighting factors representing the parameter correlation by using the nominal signatures in FIGS. 3(a), 3(b), 4(a), 4(b), 5(a) and 5(b) and adopting the single-layered neural network algorithm, and FIG. 7 shows the calculation results. As shown in FIG. 6, input data R is a two-dimensional matrix constructed by the nominal signatures, W is an array of the weighting factors of the artificial neural network, and P is an array of output values obtained by a function R×W+bias=P. The artificial neural network algorithm of the present invention sets a group of expected output values P', which represents theoretical output values of the neural network, while the goal of the linear artificial neural network algorithm is to minimize the differences between P and P', which can be represented as a mean square error (MSE) function as follows, $$MSE = \frac{\sum_{i=1}^{I=N}[P'_1 - P_i] \times [P'_i - P_i]}{N}.$$

So the objective of the linear artificial neural network algorithm is to minimize the MSE, while P' is an array of known continuous constants. There are fifteen input nominal signatures, of which five vary in critical dimension, of which five vary in thickness, and five vary in critical sidewall angle, so P' can be represented as:

$P'=[0\ 1\ 2\ 3\ 4\ 0\ 1\ 2\ 3\ 4\ 0\ 1\ 2\ 3\ 4]$

To reach the objective of the neural network algorithm, namely, to minimize the MSE, W will be larger in a high-correlation region (the region where the incident angle is more than 35 degrees), while W will be smaller in a low-correlation region (the region where the incident angle is less than 35 degrees), as shown in FIG. 7.

To reduce the influence of the parameter correlation, it is necessary to decrease the sampling number in the high-correlation region, and increase the sampling number in the low-correlation region. Table 1 shows the transforming rule used to realize this sampling concept:

TABLE 1

| Rank | Weighting factor | Sampling number (#/deg) | Sampling angle |
|---|---|---|---|
| 1 | $W(\theta) < -1.5 \times c \times sig + mean$ | 2 | $\theta \Rightarrow \theta - 0.3; \theta + 0.2$ |
| 2 | $-1.5 \times c \times sig + mean =< W(\theta) < 0.5 \times c \times sig + mean$ | 1 | $\theta \Rightarrow \theta$ |
| 3 | $0.5 \times c \times sig + mean < W(\theta)$ | 0 | $\theta \Rightarrow X$ |

θ denotes the incident angle, W(θ) denotes the weighting factors, c denotes a experience constant, and mean denotes the mean of the weighting factors, wherein the experience constant c can be an arbitrary number between 0.5 to 2.5. This transforming rule transforms the weighting factors $W_i$ calculated by the neural network into the sampling density of the measured signals, i.e. the sampling function $\theta_s$.

This sampling function divides the measured signature according to the angle of the incident light into a plurality of sub-regions (3 sub-regions), and allocates different sampling numbers to each sub-region. In other words, prior art adopts equal density sampling method, while the present invention changes the sampling numbers according to the sampling function. That is, it decreases the sampling number in the high-correlation regions, and increases the sampling numbers in the low-correlation regions.

Figure 8:
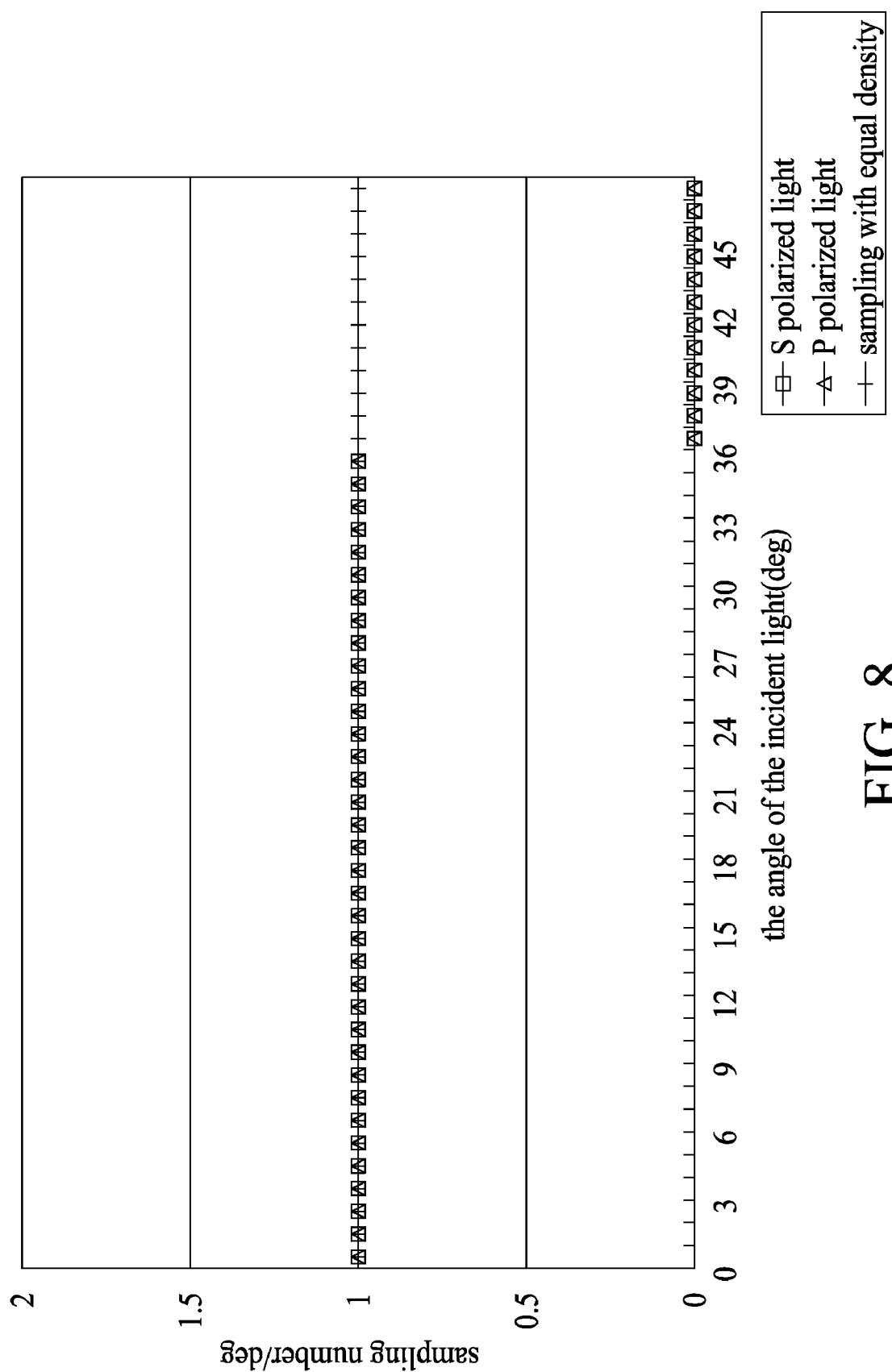
FIG. 8 shows the relationship between the sampling number and the angle of the incident light.

FIG. 8 shows the relationship between the sampling number and the angle of the incident light. The conventional equal density sampling method acquires all of the measured signals between 0 degrees and 47 degrees regardless of the type of the polarized light, e.g. s-polarized light or p-polarized light. In contrast, the present invention does not acquire the measured signals of the s-polarized light or the p-polarized light with an incident angle larger than 35 degrees, in which the correlation is higher. Subsequently, the present invention updates the nominal signatures according to the sampling function $\theta_s$ to build a signature database, updates the measured signature, compares the nominal signatures with the measured signature, and determines the values of the structural parameters of the sample 10, as described in detail as follows.

Tables 2 and 3 show the values of the structural parameters of the sample 10 measured 10 times repeatedly by the scatterometer 20 using a method of prior art with samples of equal density, and using the method of the present invention with samples generated by using a sampling function. Table 2 and 3 respectively list the values of the standard deviations of each parameter multiplied by three and the MSEs, i.e. the errors between the nominal signatures of the final results and the measured signature. Comparing Table 2 to Table 3, it can be seen that the standard deviations of each parameter multiplied by three as measured by the method of present invention are smaller than that of prior art, wherein the accuracy of the most important parameter, critical dimension, has been improved almost three times. According to the report of the semiconductor manufacturing inspection technique on international technology roadmap for semiconductors, ITRS, 2005, when the measuring accuracy improves by a factor of three, the semiconductor critical dimension measuring technique will advances two generation forward.

TABLE 2

The comparison results values of the parameters as measured by using the traditional sampling method

|  | Thickness (nm) | Critical dimension (nm) | Sidewall angle (deg) | MSE |
|---|---|---|---|---|
| #1 | 44.73 | 370.15 | 108.70 | 0.000872 |
| #2 | 44.73 | 370.15 | 108.70 | 0.000886 |
| #3 | 44.73 | 370.15 | 108.70 | 0.000888 |
| #4 | 44.61 | 372.40 | 108.70 | 0.000896 |
| #5 | 44.73 | 376.90 | 103.10 | 0.000884 |
| #6 | 44.73 | 370.15 | 108.70 | 0.000908 |
| #7 | 44.61 | 372.40 | 108.70 | 0.000896 |
| #8 | 44.61 | 372.40 | 108.70 | 0.000902 |
| #9 | 44.61 | 372.40 | 108.70 | 0.000924 |
| #10 | 44.61 | 372.40 | 108.70 | 0.000933 |
| Standard deviation × 3 | 0.190 | 6.20 | 5.31 | |
| | | | Mean | 0.000901822 |

TABLE 3

The comparison results values of the parameters as measured by using the method of the present invention

|  | Thickness (nm) | Critical dimension (nm) | Sidewall angle (deg) | MSE |
|---|---|---|---|---|
| #1 | 45.09 | 394.90 | 82.10 | 0.000872 |
| #2 | 45.09 | 394.90 | 82.10 | 0.000886 |
| #3 | 45.09 | 394.90 | 82.10 | 0.000888 |
| #4 | 45.09 | 394.90 | 82.10 | 0.000896 |
| #5 | 44.97 | 397.15 | 82.10 | 0.000884 |
| #6 | 45.09 | 394.90 | 82.10 | 0.000908 |
| #7 | 45.09 | 394.90 | 82.10 | 0.000896 |
| #8 | 45.09 | 394.90 | 82.10 | 0.000902 |
| #9 | 45.09 | 394.90 | 82.10 | 0.000924 |
| #10 | 45.09 | 394.90 | 82.10 | 0.000933 |
| Standard deviation × 3 | 0.114 | 2.13 | 0.00 | |
| | | | Mean | 0.000899 |

Furthermore, FIGS. 3(a), 3(b), 4(a), 4(b), 5(a) and 5(b) show that the correlation between the structural parameters are quite high, which may easily result in an incorrect measurement when comparing the signatures due to compensation effects between the structural parameters. Table 2 shows the signature comparison results as measured by the conventional sampling method, wherein the sidewall angle is 108 degrees. However, the sample 10 was prepared by the dry etching technique, so it is obviously not reasonable for the sidewall angle to be more than 90 degrees. This is the result of the wrong measurement caused by the compensation effects between the structural parameters.

Figure 9:
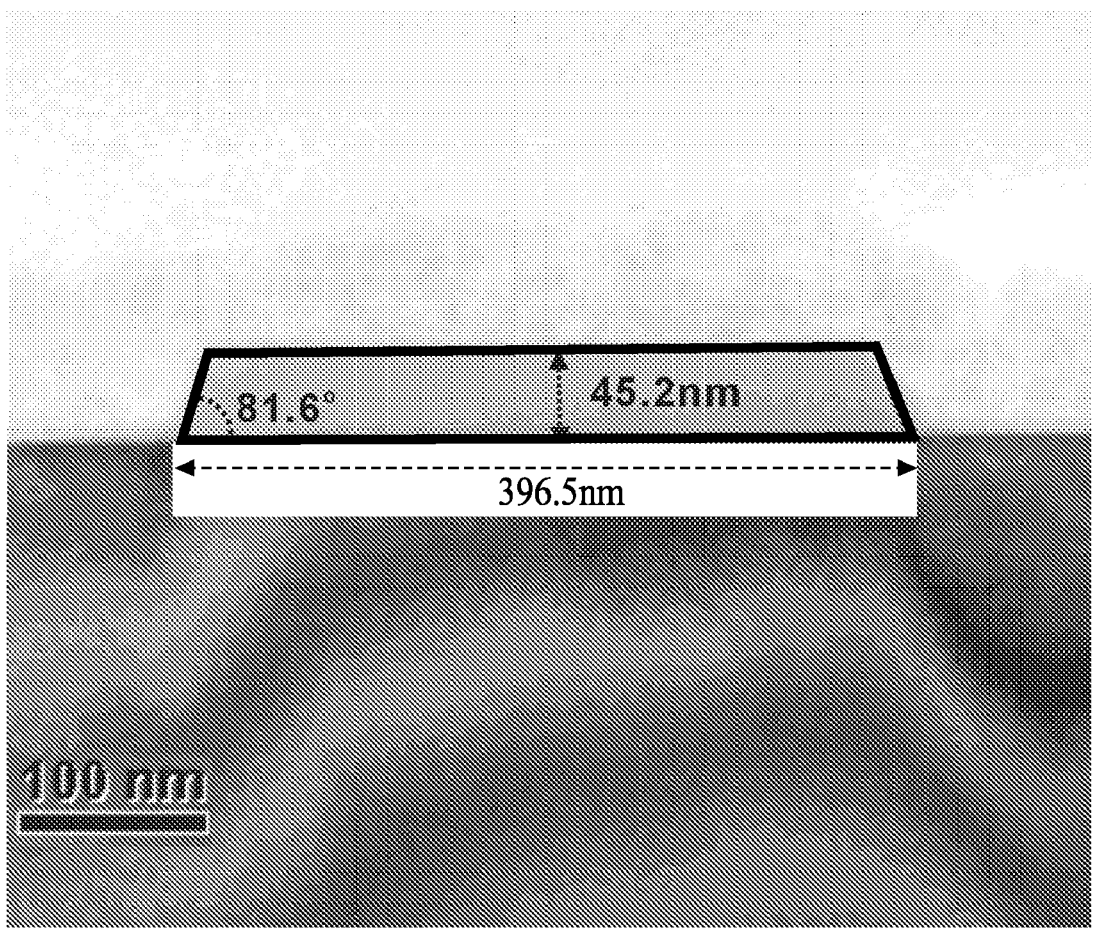
FIG. 9 shows a sidewall contour of a cross section of the sample observed by a tunneling electron microscope.

FIG. 9 shows a sidewall profile of the sample 10 observed by a tunneling electron microscope. FIG. 9 corresponds to the results of Table 3. The sidewall angle of the sample 10 is smaller than 90 degrees, wherein the observed sidewall angle is 81.6 degrees, the thickness is 45.2 nm, and the critical dimension is 396.5 nm. This demonstrates that the sampling technique of the present invention avoids the high-correlation regions and largely reduces the possibility of an incorrect measurement caused by the effects of compensation between the structural parameters. More specifically, the sampling technique of the present invention uses a sampling range of the angle of the incident light that is between −35 degrees and 35 degrees. Compared with the sampling range of the angle of the incident light according to the conventional sampling technique, which is from −47 degrees to 47 degrees, the total sampling number in the present invention is only three fourths of that of prior art. It not only reduces the time and space needed to build a signature database, but also improves the comparison time of the measured signal and the nominal signatures.

The problem of the parameter correlation directly affects the measuring performance of multi-parameter inspection systems. The present method decreases the sampling density of the measured signal in the high-correlation regions and increases such sampling density in the low-correlation regions to reduce the influence of the parameter correlation. More specifically, the present invention does not follow the conventional method of sampling the measured signal in equal density. In other words, the sampling method used in the today's industry does not take the parameter correlation into consideration, and blindingly sample the measured signals regularly in the equal densities.

To solve the problem of parameter correlation in multi-parameter inspection systems, the present invention uses a artificial neural network algorithm to automatically calculate the weighting factors of the parameter correlation in different regions of the measured signal, such as a spectral signal, and rearranges the sampling density of the measured signal according to the weighting factors to reduce the measuring error in multi-parameter inspection systems. Therefore, the present invention enhances the measurement capability of multi-parameter inspection systems and satisfies the demand in academia and in the inspection device industry for more accuracy and higher precision.

The above-described embodiments of the present invention are intended to be illustrative only. Those skilled in the art may devise numerous alternative embodiments without departing from the scope of the following claims.

What is claimed is:

1. A method for enhancing the measurement capability of multi-parameter inspection systems, comprising:

performing a measuring procedure to acquire a measured signature of a sample;

calculating a plurality of weighting factors representing a correlation between structural parameters of the sample by using a weighting algorithm;

transforming the weighting factors into a sampling function by using a transforming rule;

updating the measured signature to form an updated measured signature and a plurality of updated nominal signatures according to the sampling function;

comparing the updated measured signature and the nominal signatures to determine the structural parameters of the sample; and wherein the weighting algorithm is a linear artificial neural network algorithm.

2. The method for enhancing the measurement capability of multi-parameter inspection systems of claim 1, wherein the weighting factors are larger in high-correlation regions than those in low-correlation regions.

3. The method for enhancing the measurement capability of multi-parameter inspection systems of claim 1, further comprising a step of updating sampling numbers according to the sampling function.

4. The method for enhancing the measurement capability of multi-parameter inspection systems of claim 3, wherein the sampling function decreases the sampling numbers in the high-correlation regions.

5. The method for enhancing the measurement capability of multi-parameter inspection systems of claim 3, wherein the sampling function increases the sampling numbers in the low-correlation regions.

6. The method for enhancing the measurement capability of multi-parameter inspection systems of claim 1, wherein the sampling function divides the measured signature into a plurality of sub-regions based on the weighting factors, and allocates different sampling numbers to each sub-region.

7. The method for enhancing the measurement capability of multi-parameter inspection systems of claim 1, wherein the measured signature is a relation curve of an incident angle of an incident light and an intensity of a zero order diffraction light.

8. The method for enhancing the measurement capability of multi-parameter inspection systems of claim 1, wherein the nominal signatures are generated according to the values of the structural parameters of the sample.

9. The method for enhancing the measurement capability of multi-parameter inspection systems of claim 1, wherein the nominal signatures include s-polarized light and p-polarized light signatures.

10. The method for enhancing the measurement capability of multi-parameter inspection systems of claim 1, wherein the structural parameters are thicknesses, critical dimensions and sidewall angles of gratings.

11. A method for enhancing the measurement capability of multi-parameter inspection systems, comprising:
   performing a measuring procedure to acquire a measured signature of a sample;
   calculating a plurality of weighting factors representing a correlation between structural parameters of the sample by using a weighting algorithm;
   generating a sampling function with sampling numbers corresponding to the weighting factors;
   performing another measuring procedure to acquire an updated measured signature of the sample and generating a plurality of nominal signatures according to the sampling numbers of the sampling function;
   comparing the updated measured signature and the nominal signatures to determine structural parameters of the sample; and
   wherein the weighting algorithm is a linear artificial neural network algorithm.

12. The method for enhancing the measurement capability of multi-parameter inspection systems of claim 11, wherein the step of generating a sampling function with sampling numbers corresponding to the weighting factors comprises:
   calculating the weighting factors representing the correlation between the structural parameters of the sample by using the weighting algorithm; and
   transforming the weighting factors into the sampling function by using a transforming rule.

13. The method for enhancing the measurement capability of multi-parameter inspection systems of claim 12, wherein the weighting factors in high-correlation regions are larger than those in low-correlation regions.

14. The method for enhancing the measurement capability of multi-parameter inspection systems of claim 11, further comprising a step of updating the sampling numbers according to the sampling function.

15. The method for enhancing the measurement capability of multi-parameter inspection systems of claim 14, wherein the sampling function decreases the sampling numbers in the high-correlation regions.

16. The method for enhancing the measurement capability of multi-parameter inspection systems of claim 14, wherein the sampling function increases the sampling numbers in the low-correlation regions.

17. The method for enhancing the measurement capability of multi-parameter inspection systems of claim 11, wherein the sampling function divides the measured signature into a plurality of sub-regions based on the weighting factors, and allocates different sampling numbers to each sub-region.

18. The method for enhancing the measurement capability of multi-parameter inspection systems of claim 11, wherein the measured signature is a relation curve of an incident angle of an incident light and an intensity of a zero order diffraction light.

19. The method for enhancing the measurement capability of multi-parameter inspection systems of claim 11, wherein the nominal signatures are generated according to the values of the structural parameters of the sample.

20. The method for enhancing the measurement capability of multi-parameter inspection systems of claim 11, wherein the nominal signatures include s-polarized light and p-polarized light signatures.

21. The method for enhancing the measurement capability of multi-parameter inspection systems of claim 11, wherein the structural parameters of the sample are thicknesses, critical dimensions, and sidewall angles of gratings.

22. A multi-parameter inspection system, comprising:
   a nominal signature-generating module configured to generate a plurality of nominal signatures according to predetermined values of structural parameters of a sample;
   a calculating module configured to calculate weighting factors representing a correlation between the structural parameters of the sample;
   a sampling module configured to update a sampling number according to the weighting factors;
   a measuring module configured to acquire a measured signature of the sample according to the sampling number;
   a comparing module configured to determine the structural parameters of the sample according to the measured signature and the nominal signatures; and
   wherein the calculating module calculates the weighting factors according to a linear artificial neural network algorithm.

23. The multi-parameter inspection system of claim 22, wherein the weighting factors calculated by the calculating module are larger in high-correlation regions than in low-correlation regions.

24. The multi-parameter inspection system of claim 22, wherein the sampling module decreases the sampling numbers in high-correlation regions.

25. The multi-parameter inspection system of claim 22, wherein the sampling module increases the sampling numbers in low-correlation regions.

26. The multi-parameter inspection system of claim 22, wherein the sampling module divides the measured signature into a plurality of sub-regions based on the weighting factors, and allocates different sampling numbers to each sub-region.

27. The multi-parameter inspection system of claim 22, wherein the measured signature is a relation curve of an incident angle of an incident light and an intensity of a zero order diffraction light.

28. The multi-parameter inspection system of claim 22, wherein the nominal signatures are generated according to the nominal values of the structural parameters of the sample.

29. The multi-parameter inspection system of claim 22, wherein the nominal signatures include s-polarized light and p-polarized light signatures.

30. The multi-parameter inspection system of claim 22, wherein the structural parameters are thickness, critical dimension, and sidewall angle of gratings.

* * * * *

UNITED STATES PATENT AND TRADEMARK OFFICE
CERTIFICATE OF CORRECTION

| | | |
|---|---|---|
| PATENT NO. | : 7,610,170 B2 | Page 1 of 1 |
| APPLICATION NO. | : 11/858442 | |
| DATED | : October 27, 2009 | |
| INVENTOR(S) | : Chun Hung Ko, Yi Sha Ku and Chung Chu Chang | |

It is certified that error appears in the above-identified patent and that said Letters Patent is hereby corrected as shown below:

Title page, item [75] second inventor's name should be as follows: Yi Sha Ku

Signed and Sealed this

Twenty-ninth Day of December, 2009

David J. Kappos
*Director of the United States Patent and Trademark Office*